United States Patent
Fernandes et al.

(10) Patent No.: US 8,734,815 B2
(45) Date of Patent: May 27, 2014

(54) VACCINE COMPOSITION AND IMMUNIZATION METHOD

(75) Inventors: Ana Paula Salles Moura Fernandes, Belo Horizonte MG (BR); Christiane De Freitas Abrantes, Belo Horizonte MG (BR); Eduardo Antonio Ferraz Coelho, Belo Horizonte MG (BR); Ricardo Tostes Gazzinelli, Belo Horizonte MG (BR)

(73) Assignee: Universidade Federal de Minas Gerais, Belo Horizonte (BR)

( * ) Notice: Subject to any disclaimer, the term of this patent is extended or adjusted under 35 U.S.C. 154(b) by 969 days.

(21) Appl. No.: 12/374,626

(22) PCT Filed: Jul. 20, 2007

(86) PCT No.: PCT/BR2007/000248
§ 371 (c)(1),
(2), (4) Date: Oct. 8, 2009

(87) PCT Pub. No.: WO2008/009088
PCT Pub. Date: Jan. 24, 2008

(65) Prior Publication Data
US 2011/0008391 A1    Jan. 13, 2011

(30) Foreign Application Priority Data
Jul. 21, 2006    (BR) .................................... 0603490

(51) Int. Cl.
*A61K 39/00* (2006.01)
(52) U.S. Cl.
USPC ................ 424/269.1; 424/185.1; 530/350
(58) Field of Classification Search
CPC .................................................... A61K 39/008
USPC ......................................................... 424/269.1
See application file for complete search history.

(56) References Cited

U.S. PATENT DOCUMENTS

| | | | | |
|---|---|---|---|---|
| 5,733,778 A * | 3/1998 | Matlashewski et al. | ... | 435/320.1 |
| 5,780,591 A * | 7/1998 | Matlashewski et al. | ...... | 530/350 |
| 6,375,955 B1 * | 4/2002 | Reed et al. | ................ | 424/269.1 |
| 6,485,726 B1 * | 11/2002 | Blumberg et al. | .......... | 424/178.1 |
| 6,875,584 B1 * | 4/2005 | Tarleton et al. | ............... | 435/69.1 |
| 7,264,810 B2 * | 9/2007 | Renner et al. | ............... | 424/185.1 |
| 2001/0034330 A1 * | 10/2001 | Kensil | .............................. | 514/44 |

(Continued)

FOREIGN PATENT DOCUMENTS

| | | | | |
|---|---|---|---|---|
| WO | 95/06729 | * | 3/1995 | ............. C12N 15/30 |
| WO | 02/078735 | * | 10/2002 | ............ A61K 39/008 |
| WO | 2006/110915 | * | 10/2006 | ............ C12N 15/09 |

OTHER PUBLICATIONS da Silva, B.P. et al, Vaccine, vol. 23(8), pp. 1061-1071, 2005, *Pulcherrima saponin*, from the leaves of *Calliandra pulcherrima*, as adjuvant for immunization in the murine model of visceral leishmaniasis.*

(Continued)

*Primary Examiner* — Albert Navarro
*Assistant Examiner* — Ginny Portner
(74) *Attorney, Agent, or Firm* — Nixon & Vanderhye PC

(57) ABSTRACT

The present invention refers to the recombinant vaccine against canine visceral leishmaniasis containing the recombinant A2 protein and saponin, as an adjuvant, allowing the distinction between vaccinated and infected animals through conventional ELISA or immunofluorescence tests that employ antigens of promastigote forms of *Lesihmania*.

17 Claims, 13 Drawing Sheets

(56) References Cited

U.S. PATENT DOCUMENTS

| | | | |
|---|---|---|---|
| 2002/0028215 A1* | 3/2002 | Kadurugamuwa et al. | 424/234.1 |
| 2002/0037290 A1* | 3/2002 | Armen | 424/178.1 |
| 2003/0175294 A1* | 9/2003 | Skeiky et al. | 424/190.1 |
| 2004/0170636 A1* | 9/2004 | Matlashewski | 424/184.1 |
| 2006/0051364 A1* | 3/2006 | Valenzuela et al. | 424/190.1 |
| 2007/0184046 A1* | 8/2007 | Costa et al. | 424/94.6 |
| 2008/0226670 A1* | 9/2008 | Dominowski et al. | 424/201.1 |
| 2009/0028932 A1* | 1/2009 | Wilson et al. | 424/450 |
| 2009/0291099 A1* | 11/2009 | Goto et al. | 424/192.1 |

OTHER PUBLICATIONS

Coelho, Eduardo Antonio Ferraz et al, Infection and Immunity, 2003, vol. 71(7), pp. 3988-3994, Immune responses induced by the *Leishmania donovani* A2 antigen, but Not the LACK antigen, are protective against Experimental *Leishmania amazonensis* Infection.*

Int'l Search Report for PCT/BR2007/000248, mailed Mar. 14, 2008.

Written Opinion for PCT/BR2007/000248, mailed Mar. 14, 2008.

Charest et al. "Developmental gene expression in *Leishmania donovani*: Differential cloning and analysis of an amastigote-stage-specific gene" Mol. Cell. Biol. 14:2975-2984 (1994).

Coler et al. "Second-generation vaccines against leishmaniasis" *Trends in Parasitology*, vol. 21, No. 5, pp. 244-249 (May 2005).

Ghosh et al. "Immunization with A2 protein results in a mixed Th1/Th2 and a humoral response which protects mice against *Leishmania donovani* infections" *Vaccine*, vol. 20 Nos. 1-2, pp. 59-66 (Oct. 2001).

Porrozzi et al. "Comparative evaluation of enzyme-linked immunosorbent assays based on crude and recombinant Leishmanial antigens for serodiagnosis of symptomatic and asymptomatic *Leishmania infantum* visceral infections in dogs" Clinical and Vaccine Immunology, vol. 14, No. 5, pp. 544-548 (May 2007).

Teodoro Da Costa et al. "Standardization of a rapid immunochromatographic test with the recombinant antigens K39 and K26 for the diagnosis of canine visceral leishmaniasis" Transactions of the Royal Society of Tropical Medicine and Hygiene, vol. 97, No. 6, pp. 678-682 (Nov. 2003).

Search report for European Application No. 07800392.8, mailed Mar. 26, 2010, pp. 1-8.

* cited by examiner

SEQUENCE LISTING

<160> NUMBER OF SEQ ID NOS: 2

<210> SEQ ID NO 1
<211> LENGTH: 2817
<212> TYPE: DNA
<213> ORGANISM: Leishmania (donovani) infantum

<400> SEQUENCE: 1

```
gagctccccc agcgaccctc tcggcaacgc gagcgcccca gtccccccac gcacaacttt      60
gaccgagcac aatgaagatc cgcagcgtgc gtccgcttgt ggtgttgctg gtgtgcgtcg     120
cggcggtgct cgcactcagc gcctccgctg agccgcacaa ggcggccgtt gacgtcggcc     180
cgctctccgt tggcccgcag tccgtcggcc cgctctctgt tggcccgcag gctgttggcc     240
cgctctccgt tggcccgcag tccgtcggcc cgctctctgt tggcccgcag gctgttggcc     300
cgctctctgt tggcccgcag tccgttggcc cgctctccgt tggcccgctc tccgttggcc     360
cgcagtctgt tggcccgctc tccgttggct cgcagtccgt cggcccgctc tctgttggtc     420
cgcagtccgt cggcccgctc tccgttggcc cgcaggctgt tggcccgctc tccgttggcc     480
cgcagtccgt cggcccgctc tctgttggcc cgcaggctgt tggcccgctc tctgttggcc     540
cgcagtccgt tggcccgctc tccgttggcc cgcagtctgt tggcccgctc tccgttggct     600
cgcagtccgt cggcccgctc tctgttggtc cgcagtccgt cggcccgctc tccgttggcc     660
cgcagtctgt cggcccgctc tccgttggcc cgcagtccgt cggcccgctc tccgttggtc     720
cgcagtccgt tggcccgctc tccgttggcc cgcagtccgt tgacgtttct ccggtgtctt     780
aaggctcggc gtccgctttc cggtgtgcgt aaagtatatg ccatgaggca tggtgacgag     840
gcaaaccttg tcagcaatgt ggcattatcg tacccgtgca agagcaacag cagagctgag     900
tgttcaggtg gccacagcac cacgctcctg tgacactccg tggggtgtgt gtgaccttgg     960
ctgctgttgc caggcggatg aactgcgagg gccacagcag cgcaagtgcc gcttccaacc    1020
ttgcgacttt cacgccacag acgcatagca gcgccctgcc tgtcgcggcg catgcgggca    1080
```

```
agccatctag atgcgcctct ccacgacatg gccggaggcg gcagatgaag gcagcgaccc    1140
cttttccccg gccacgacgc cgcgctgagg cgggccccac agcgcagaac tgcgagcgcg    1200
gtgcgcgggc gctgtgacgc acagccggca cgcagcgtac cgcacgcaga cagtgcatgg    1260
ggaggccgga ggagcaagag cggtggacgg gaacggcgcg aagcatgcgg cacgccctcg    1320
atgtgcctgt gtgggctgat gaggcgcgga tgccggaagc gtggcgaggg catcccgagt    1380
tgcaccgtcg agtcctccag gcccgaatgt ggcgagcctg cggggagcag attatgggat    1440
gcggctgctc gaagcgaccg agggcgctga ccggaaggtg gcccacttcc tcctcgggcc    1500
tgtgcggcat ccgccctcga tcgggagccc gaatggtggc cgcgcgggtg aaggcgtgcc    1560
gcccacccgc gtctccgtgt ggcgccgctg ggggcaggtg cgctgtggct gtgtatgtgc    1620
gctgatgtgc tgacttgttc gtggtgggct atgggcacgg tgaggggcga cgttggccct    1680
tgctgacttc ctctgctttc ttattattct cagtgccccc gctggattgg gctgcatcgg    1740
cggtctgtat cgcgcttgtc tctctcattt gacggctgcg cgcctcccgc ccctcccact    1800
cgtgctgtgg gatggaggca cggccgggct ctgtgttgtg tgcaccgcgt gcaagaattc    1860
agatgaggga ctgccgagcg agcagacaaa gcagcagcag caacaggaag gcaggcctga    1920
gcacgttttc ttttctctct tgagactgcg gactacggga atcagagacg tcgtcagaga    1980
cgcgcatccg cacccgcgcg ctatgcttcc tcgttctctc tcccgcccca ttctgtgcgc    2040
ctgcctgtct gcgtgtcgcg agcgccgttg ccggcggtct ctctcccctc ccttcgcttc    2100
tctcttgcaa gcgcttcctt tttcacagcc gaacgttgct gctcgcctgg aggccgttcc    2160
ccctcttatc atctctgcat ttattttttac acgtgctttt gctttggctt cctgacgatg    2220
ccggccacct caccgcggtg tcagggccca gcgcccactc tttgtgggca ggccaagtag    2280
cctgcagcct gcccatgagc acggctgtgg actcttggtg ccagcggaca ggtgtgggct    2340
ggcgctgtgc cggtgacacc aacggtcatg atgacgcttg gaccagctca ctgcggatca    2400
tgccgacgat tcaacgaatg cgcgcatcca cctactgcct ttctgccttt gctgcgctgc    2460
ggtggtgctg agcgtggtcc cggggcctag cctgcgctgt acgcagcggc attgcggtgg    2520
gctgagcggc gccaggcggt gctggccggc cctgctgctt ggcatagccg tggcgtgcag    2580
cagatgcgga tgggctgtgg ctgcgcatgc gtgtgtgcgt tgacttgttc gtggtgggcg    2640
ggcacgtaaa cggcaaaatg cgctttggcg ttccggcgcc acgctccggc gctggtgcgg    2700
tattcgaata cgcgcctgaa gaggtggcga ggaaaatggc acgaggcgca gagggaaaaa    2760
acgaaaagtg caaagtgcgc aaaccgcgca gaaaatgcgg gaaaaacgaa aagtgca       2817
```

<210> SEQ ID NO 2
<211> LENGTH: 236
<212> TYPE: PRT
<213> ORGANISM: Leishmania (donovani) infantum

<400> SEQUENCE: 2

Met Lys Ile Arg Ser Val Arg Pro Leu Val Val Leu Leu Val Cys Val
1               5                   10                  15

Ala Ala Val Leu Ala Leu Ser Ala Ser Ala Glu Pro His Lys Ala Ala
            20                  25                  30

Val Asp Val Gly Pro Leu Ser Val Gly Pro Gln Ser Val Gly Pro Leu
        35                  40                  45

Ser Val Gly Pro Gln Ala Val Gly Pro Leu Ser Val Gly Pro Gln Ser
    50                  55                  60

Val Gly Pro Leu Ser Val Gly Pro Gln Ala Val Gly Pro Leu Ser Val
65                  70                  75                  80

-continued

```
Gly Pro Gln Ser Val Gly Pro Leu Ser Val Gly Pro Leu Ser Val Gly
                 85                  90                  95

Pro Gln Ser Val Gly Pro Leu Ser Val Gly Ser Gln Ser Val Gly Pro
            100                 105                 110

Leu Ser Val Gly Pro Gln Ser Val Gly Pro Leu Ser Val Gly Pro Gln
        115                 120                 125

Ala Val Gly Pro Leu Ser Val Gly Pro Gln Ser Val Gly Pro Leu Ser
    130                 135                 140

Val Gly Pro Gln Ala Val Gly Pro Leu Ser Val Gly Pro Gln Ser Val
145                 150                 155                 160

Gly Pro Leu Ser Val Gly Pro Gln Ser Val Gly Pro Leu Ser Val Gly
                165                 170                 175

Ser Gln Ser Val Gly Pro Leu Ser Val Gly Pro Gln Ser Val Gly Pro
            180                 185                 190

Leu Ser Val Gly Pro Gln Ser Val Gly Pro Leu Ser Val Gly Pro Gln
        195                 200                 205

Ser Val Gly Pro Leu Ser Val Gly Pro Gln Ser Val Gly Pro Leu Ser
    210                 215                 220

Val Gly Pro Gln Ser Val Asp Val Ser Pro Val Ser
225                 230                 235
```

VACCINE COMPOSITION AND IMMUNIZATION METHOD

This application is the U.S. national phase of International Application No. PCT/BR2007/000248, filed 20 Jul. 2007, which designated the U.S. and claims priority to BR Application No. PI0603490-0, filed 21 Jul. 2006, the entire contents of each of which are hereby incorporated by reference.

The present invention refers to the recombinant vaccine against canine visceral leishmaniasis containing the recombinant A2 protein and saponin, as an adjuvant, allowing the distinction between vaccinated and infected animals through conventional ELISA or immunofluorescence tests that employ antigens of promastigote forms of *Leishmania*.

The many leishmaniasis constitute a group of parasitical diseases that clinically present themselves as cutaneous or mucocutaneous wounds, or in the form of a visceral infection. They occur due to the infection by a variety of protozoan species belonging to the genus *Leishmania* (World Health Organization. Program for the surveillance and control of leishmaniasis. www dot who dot int slash emc slash diseases slash leish slash index dot html 2005). The many leishmaniasis are endemic in about eighty-eight countries. Of these, seventy-two are developing countries, and in this group are included thirteen of the countries with the lowest development rate in the world. The visceral form occurs due to infections caused by the species *Leishmania* (*Leishmania*) *donovani* and *L.* (*L.*) *infantum* in countries of Europe, Asia, Africa and the Middle-east, and due to the specie *L.* (*L.*) *chagasi* in Latin American countries (DESJEUX, P. Comp. Immunol. Microbiol. Infect. Dis.: 27, 2004). Alterations in the functions of the spleen, the liver and the bone marrow are observed on infected patients, and the infection may become chronic, causing irregular long-lasting fever, hepatosplenomegaly, lymphadenopathy, anaemia, leucopeny, oedema, progressive enfeeblement and weight-loss, and possibly causing death if treatment is not administered. Infected individuals may also remain asymptomatic, though 20% of the individuals in endemic regions develop the classic form of the disease. The symptoms are progressive, and complications deriving from the infection's evolution are responsible for the greater part of the deaths (SUNDAR, S. & RAI, M. Clin. Diagn. Lab. Immunol., 9: 2002).

*L.* (*L.*) *chagasi* has got vast geographic distribution in the Americas, being found in Brazil, Argentina, Colombia, Bolivia, El Salvador, Guatemala, Honduras, Mexico, Paraguay, and Venezuela. Species such as marsupials and skunks are well-known wild reservoirs of the parasite. In domestic environments, the dog is considered the main reservoir in the domestic transmission cycle of visceral leishmaniasis (VL), due to the high prevalence of the canine infection as compared to the human one. Infected dogs, even the asymptomatic ones, present a great quantity of parasites in the skin, facilitating the infection of the vector insect from this reservoir, and, consequently, the transmission of the disease to people (TESH, R. *Am. J. Med. Hyg.:* 52, 1995).

Canine VL treatment, whichever the medicine used, is not viable as a measure for the control of the disease, for it is costly. Moreover, treated and clinically cured dogs frequently display returns of the disease, remaining as infection sources for the vector, and it raises the chance of selecting lineages that are resistant to such medicines, with serious implications for human treatment (GRAMICCIA, M. & GRADONI, L. *Int. J. Parasitol.* 35: 2005).

This fact, associated to the lethalness of human VL when not treated, has taken the World Health Organization (WHO) to profess the elimination of dogs when they are seropositive for *Leishmania* antigens, as a measure for Public Health organizations controlling the disease. In this way, Brazil's Health Ministry adopted such procedure. Therefore, one of the most used actions in VL control is the elimination of infected dogs, which are detected through serological diagnosis or by the presence of clinical symptoms. However, such procedures bring deep sadness and indignation to their owners, who, many times, prefer omitting the disease to the competent organizations until the animals are near their deaths, when they become important transmitters of the parasite (TESH, R. *Am. J. Med. Hyg.:* 52, 1995).

Most researches on vaccine development are based on the identification of molecules of the parasite and in immunisation protocols that can induce Th1 cellular immune response, an essential requirement for inducing protection to the disease. Among dogs, the resistance or susceptibility to the disease is, probably, also associated to the dichotomy of the Th1/Th2 response. The resistance is associated to high specific lymphoproliferative response and with positive delayed hypersensitivity reaction (DHR), besides low quantity of parasite-specific antibodies. Resistance to the infection and protection, among dogs, would be related to a high interferon-gamma (IFN-γ) and nitric oxide (NO) production, and to the leishmanicidal activity of the parasite-infected macrophages, which means a Th1 immune response profile. High levels of IgG1 antibodies would be related to susceptibility, while high levels of IgG2a would be associated to resistance (Moreno, J. & Alvar, J. *Trends Parasitol.:* 18, 2002; Molano, I. et al., *Vet. Immunol. Parasitol.:* 92, 2003). Therefore, in studies which assess vaccine effectiveness against infection by *Leishmania*, IFN-γ and IgG2 (dogs) or IgG2a (mice) antibodies are used as Th1 response markers and resistance-inductor markers. Interleucine-4, interleucine-10 and IgG2 (dogs) or IgG2a (mice) antibodies, on the other hand, are used as Th2 answer and susceptibility markers.

Vaccines against canine Leishmaniasis are hard to develop, and due to this are still rare. One canine vaccine is available, Leishmune®. It uses as its vaccine active principle a purified antigenic complex, including proteins, that corresponds to the Fucose-Mannose Ligand (FML), present in the parasite's surface, according to the national patent request n° PI 9302386-3 (composition containing fractions of *Leishmania* cells called fml antigen, "fucose-mannose ligand" or "fucose-mannose connecter", use of the fml antigen and its subfractions and components for applications in immunodiagnosis specific to human and animal visceral leishmaniasis, for applications in vaccines and for treatment or immunotherapy against human and canine visceral leishmaniasis).

Leishmune®'s primary characteristic is the induction of humoural response. The vaccinated dog rapidly develops a response through the production of specific antibodies against the parasite. Many tests, presented by the mentioned vaccine's inventor and partners, show that the vaccine protects approximately 86% of the animals which received it when placed in endemic areas. These studies' results were questioned by the scientific community, as well as by the industry, since the control and the vaccinated animals were located in different cities. Another important failure of the mentioned test was the presence of dogs, in both groups, using insect-repellent-impregnated collars. The parasite is transmitted by an insect's sting, and if the contact with the vector insect is deterred by use of repellent collars the dog is not really exposed to the alleged natural challenge. Based on the above data, the described protection percentage is questionable. Therefore, other studies have been carried out and some are being carried out by request of the public health regulatory organization.

Particularly, in what pertains to public health, it is known that according to WHO regulations seropositive animals must be sacrificed. It is also known that this measure is adopted in Brazil. Once having received this vaccine, the animal will develop heavy response through antibodies specific to the parasite, becoming seropositive. The diagnosis professed by the public organizations is the serologic one, due to it being cheap and easily executable, thus capable of being applied to all regions of the country without further problems. The vaccinated dogs must be sacrificed.

The indistinction, by traditional methods, of infected animals from vaccinated ones, simply creates a great public health problem. The owners of vaccinated animals show the vaccine card and do not allow the animal to be sacrificed. Taking into account that for each one hundred animals which received the vaccine, about fourteen may become infected, leading to an increase in the amount of possible domestic leishmaniasis reservoirs. Another important issue is related to epidemiologic inquiries made by the Ministry of Health, which are an important form of identifying the evolution of the disease in different regions. This inquiry is partially based on the serologic results of the dogs. With the advent of Leishmune® vaccination the obtained results are not real, for seropositive animals may not be infected, but merely vaccinated. It is possible to distinguish between dogs that are seropositive due to vaccination or due to infection by exams that detect the parasite's presence, such as Polymerase Chain Reaction (PCR) or immunocytochemistry. However, to perform these tests, requires fine techniques and costly equipment and reagents, besides trained technicians, in order to guarantee the accuracy of the results. PCR is done in private clinics; its use in public health is hard to be implemented and of elevated financial cost.

In addition to this, Leishmune® has got high production costs, arriving at the market at prices that make it impossible for the whole population to have access to it. It is known that Brazil has a large low income population, and these people do not have access to the mentioned product. As this is a disease that expands itself in many regions of the country, it is ever more important to adopt measures that hinder the continuity of the parasite's transmission, especially the infection of dogs that live in domestic or adjoining areas. The possible use of this product in public health campaigns would be costly, besides the aforementioned problems. Leishmune® presents interesting immunologic characteristics, but goes against the control measures adopted for the current epidemic, deterring the sacrifice of seropositive dogs, interfering in the epidemiologic inquiries and also being of high cost for public health usage.

The A2 antigen has been identified, initially, in the specie *L.* (*L.*) *donovani*, by Charest & Matlashewsky (*Mol. Cell. Biol.:* 14, 1994), by a library of amastigote forms of *L.* (*L.*) *donovani* cDNA. Multiple copies of the A2 gene are grouped in the *L.* (*L.*) *donovani* chromosome 22 (850 kb). These genes are maintained in the species *L.* (*L.*) *donovani, L.* (*L.*) *infantum, L.* (*L.*) *chagasi, L.* (*L.*) *amazonensis* and *L.* (*L.*) *mexicana* (Ghedin et al., *Clin. Diagn. Lab. Immunol.:* 4, 1997).

In previously conducted searches through patent banks, there were found patent requests related to the usage of the A2 antigen as a reagent for leishmaniasis vaccination, as described below. U.S. Pat. No. 5,733,778 states the nucleotide sequence of the A2 gene and claims the protection of its expression in microbial hosts. The VL9 *L.*(*L.*)*donovani* string's A2 gene sequence is deposited in Genebank, as described below (SEQ ID NO: 1):

LOCUS S69693 2817 bp mRNA linear INV Mar. 26-2002
ACCESSION S69693
VERSION S69693.1 GI:546453
ORGANISM *Leishmania* (*donovani*) *infantum*
  Eukaryota; Euglenozoa; Kinetoplastida; Trypanosomatidae; *Leishmania.*
REMARK GenBank staff at the National Library of Medicine created this
FEATURES Location/Qualifiers
  source 1.2817
    /organism="*Leishmania donovani infantum*"
    /mol_type="mRNA"
    /strain="Ethiopian LV9"
    /sub_species="*infantum*"
    /db_xref="taxon:5662"
    /dev_stage="amastigote"
  gene 1.2817
    /gene="A2"
  CDS 72.782
    /gene="A2"
    /note="*Plasmodium falciparum* S antigen homolog; This sequence comes from FIG. 5A"
    /codon_start=1
    /product="stage-specific S antigen homolog"
    /protein_id="AAB30592.1"
    /db_xref="GI:546454"
Origin

```
  1 gagctccccc agcgaccctc tcggcaacgc gagcgcccca gtccccccac gcacaacttt
 61 gaccgagcac aatgaagatc cgcagcgtgc gtccgcttgt ggtgttgctg gtgtgcgtcg
121 cggcggtgct cgcactcagc gcctccgctg agccgcacaa ggcggccgtt gacgtcggcc
181 cgctctccgt tggcccgcag tccgtcggcc cgctctctgt tggcccgcag gctgttggcc
241 cgctctccgt tggcccgcag tccgtcggcc cgctctctgt tggcccgcag gctgttggcc
301 cgctctctgt tggcccgcag tccgttggcc cgctctccgt tggcccgctc tccgttggcc
361 cgcagtctgt tggcccgctc tccgttggct cgcagtccgt cggcccgctc tctgttggtc
421 cgcagtccgt cggcccgctc tccgttggcc cgcaggctgt tggcccgctc tccgttggcc
481 cgcagtccgt cggcccgctc tctgttggcc cgcaggctgt tggcccgctc tctgttggcc
541 cgcagtccgt tggcccgctc tccgttggcc cgcagtctgt tggcccgctc tccgttggct
601 cgcagtccgt cggcccgctc tctgttggtc cgcagtccgt cggcccgctc tccgttggcc
```

-continued

```
 661 cgcagtctgt cggcccgctc tccgttggcc cgcagtccgt cggcccgctc tccgttggtc 721 cgcagtccgt tggcccgctc tccgttggcc cgcagtccgt tgacgtttct ccggtgtctt 781 aaggctcggc gtccgctttc cggtgtgcgt aaagtatatg ccatgaggca tggtgacgag 841 gcaaaccttg tcagcaatgt ggcattatcg tacccgtgca agagcaacag cagagctgag 901 tgttcaggtg gccacagcac cacgctcctg tgacactccg tggggtgtgt gtgaccttgg 961 ctgctgttgc caggcggatg aactgcgagg gccacagcag cgcaagtgcc gcttccaacc 1021 ttgcgacttt cacgccacag acgcatagca gcgccctgcc tgtcgcggcg catgcgggca 1081 agccatctag atgcgcctct ccacgacatg gccggaggcg gcagatgaag gcagcgaccc 1141 cttttccccg gccacgacgc cgcgctgagg cgggccccac agcgcagaac tgcgagcgcg 1201 gtgcgcgggc gctgtgacgc acagccggca cgcagcgtac cgcacgcaga cagtgcatgg 1261 ggaggccgga ggagcaagag cggtggacgg gaacggcgcg aagcatgcgg cacgccctcg 1321 atgtgcctgt gtgggctgat gaggcgcgga tgccggaagc gtggcgaggg catcccgagt 1381 tgcaccgtcg agtcctccag gcccgaatgt ggcgagcctg cggggagcag attatgggat 1441 gcggctgctc gaagcgaccg agggcgctga ccggaaggtg gcccacttcc tcctcgggcc 1501 tgtgcggcat ccgccctcga tcgggagccc gaatggtggc cgcgcgggtg aaggcgtgcc 1561 gcccacccgc gtctccgtgt ggcgccgctg ggggcaggtg cgctgtggct gtgtatgtgc 1621 gctgatgtgc tgacttgttc gtggtgggct atgggcacgg tgaggggcga cgttggccct 1681 tgctgacttc ctctgctttc ttattattct cagtgccccc gctggattgg gctgcatcgg 1741 cggtctgtat cgcgcttgtc tctctcattt gacggctgcg cgcctcccgc ccctcccact 1801 cgtgctgtgg gatggaggca cggccgggct ctgtgttgtg tgcaccgcgt gcaagaattc 1861 agatgaggga ctgccgagcg agcagacaaa gcagcagcag caacaggaag gcaggcctga 1921 gcacgttttc ttttctctct tgagactgcg gactacggga atcagagacg tcgtcagaga 1981 cgcgcatccg cacccgcgcg ctatgcttcc tcgttctctc tcccgcccca ttctgtgcgc 2041 ctgcctgtct gcgtgtcgcg agcgccgttg ccggcggtct ctctcccctc ccttcgcttc 2101 tctcttgcaa gcgcttcctt tttcacagcc gaacgttgct gctcgcctgg aggccgttcc 2161 ccctcttatc atctctgcat ttattttttac acgtgctttt gctttggctt cctgacgatg 2221 ccggccacct caccgcggtg tcagggccca gcgcccactc tttgtgggca ggccaagtag 2281 cctgcagcct gcccatgagc acggctgtgg actcttggtg ccagcggaca ggtgtgggct 2341 ggcgctgtgc cggtgacacc aacggtcatg atgacgcttg gaccagctca ctgcggatca 2401 tgccgacgat tcaacgaatg cgcgcatcca cctactgcct ttctgccttt gctgcgctgc 2461 ggtggtgctg agcgtggtcc cggggcctag cctgcgctgt acgcagcggc attgcggtgg 2521 gctgagcggc gccaggcggt gctggccggc cctgctgctt ggcatagccg tggcgtgcag 2581 cagatgcgga tgggctgtgg ctgcgcatgc gtgtgtgcgt tgacttgttc gtggtgggcg 2641 ggcacgtaaa cggcaaaatg cgctttggcg ttccggcgcc acgctccggc gctggtgcgg 2701 tattcgaata cgcgcctgaa gaggtggcga ggaaaatggc acgaggcgca gagggaaaaa 2761 acgaaaagtg caaagtgcgc aaaccgcgca gaaaatgcgg gaaaaacgaa aagtgca
```

U.S. Pat. No. 570,591, WO9506729, EP0716697 and MXPA03008832 report the amino acid sequence of the A2 protein. A2 is composed of a sequence of ten amino acids, repeated from forty to ninety times, depending on the "A2 family" gene that encodes it (Charest & Matlashewski. Mol. Cell. Biol.: 14, 1994; Zhang et al., Mol. Bioch. Parasitol.: 78, 1996 ), as shown below (SEQ ID NO: 2):

MKIRSVRPLVVLLVCVAAVLALSASAEPHKAAVDVGPLSVGPQSVGPLSV

GPQAVGPLSVGPQSVGPLSVGPQAVGPLSVGPQSVGPLSVGPLSVGPQSV

GPLSVGSQSVGPLSVGPQSVGPLSVGPQAVGPLSVGPQSVGPLSVGPQAV

GPLSVGPQSVGPLSVGPQSVGPLSVGSQSVGPLSVGPQSVGPLSVGPQSV

GPLSVGPQSVGPLSVGPQSVGPLSVGPQSVDVSPVS.

The patent request U.S. Pat. No. 5,780,591, besides describing the A2 native protein, i.e., describing how it is found in the parasite, claims its possible use as a vaccine or as a diagnosis antigen. The patent request U.S. Pat. No. 5,733,778 describes the DNA sequence of the A2 gene and its bacterial expression. The patent request U.S. Pat. No. 6,133,017 describes the obtainment of attenuated parasites (*Leishmania donovani*) by the deletion of the A2 gene, as well as their utilization as attenuated vaccines. The patents WO9506729, EP0716697 or MXPA03008832 are related one to another and claim the utilization of the A2 antigen in the form of a recombinant protein, DNA or attenuated parasites as a vaccine. In Brazil the patent request PI0208532 (PCT number CA0200437) was registered on INPI (National Institute of Industrial Property), under the generic title of "vacina contra *leishmania*" (vaccine against *leishmania*), which describes the invention of a DNA vaccine whose antigenic component is the A2 antigen, and also describes the processes for administering this DNA vaccine that induces immune response to *Leishmania* infection in the host to which it is administered.

The experimental evidences that supported the protection requests for the vaccines above, however, consist essentially of two vaccination studies (Ghosh et al. *Vaccine:* 19, 2001; Ghosh et al., *Vaccine:* 20, 2002). In these studies experimental models (mice) were assessed, making use of the A2 antigen under the recombinant protein associated to *Comybacterium parvum*, as an adjuvant, or in DNA form with the plasmid pcDNA3/E6. According to those studies, animals immunised with the A2 antigen and challenged with *L. donovani* have presented significant reduction of the parasite load in the liver and high production of IFN-γ and IgG2a antibodies specific to the A2 protein. Even though the vaccination with A2 DNA granted protection, the protection was more significant when the DNA was associated to the plasmid pcDNA3/E6. Albeit necessary for the validation of a vaccine formulation's efficacy, the assessment step in many experimental models cannot be considered conclusive, even when it presents positive results.

The development of a vaccine that is effective in protecting the dog and, consequently, in lowering the chances of transmission to humans, would be of great relevance for the control of leishmaniasis. In Brazil, the Health and Agriculture Ministries, according to an edict that is available to public consultation (www dot mapa dot gov dot br), profess that this vaccine, once applied to the dogs, must be able to induce an immunologic response effective in reducing tissue parasitism and the transmission of the parasite to the vector insect. This can be verified through xenodiagnosis, polymerase chain reaction (PCR) or immunohistochemistry. In addition to this, the vaccine must allow the serologic distinction between vaccinated and infected dogs while employing low-cost laboratorial methods that are available to the public network, thus not encumbering the country's Health System. Therefore, the adoption of a vaccine as a new control measure must not interfere with the current control measures.

The present invention proposes the employment of the specific amastigote A2 antigen in vaccine preparations as a solution for these aspects related to the development of a vaccine applicable to the epidemiologic context of leishmaniasis, especially in Brazil. Since it is a specific antigen of the amastigote form of various *Leishmania* species, the antibodies produced by the dogs in the vaccination process with this antigen are non-reactive to serologic diagnosis infection tests. This is due to the fact that in the laboratorial routine available to the Brazilian public health network these tests use antigens based on the promastigote form of the parasite, which is cheaper to obtain.

After many assessments and the verification of antigen A2 efficacy in inducing protection against infection by *L. chagasi* and *L. amazonensis*, the main *Leishmania* species that cause VL in Brazil, and after characterizing the immune response induced by the antigen A2 in mice, the vaccine formulation described below, to be used in dogs, was developed. The capacity of this formulation to induce adequate humoural and cellular immune response in dogs was then assessed considering that it must be adequate for use as a VL vaccine in the epidemiologic context of this disease in regions where the sacrifice of seropositive animals is adopted as a control measure. Currently, the diagnosis tests used in the public health network do not allow the serologic distinction between infected animals and those which received vaccines made of antigens of promastigote forms of the parasite. The object of this present request is a formulation which allows such distinction, since it is made of an antigen of amastigote forms of the parasite, avoiding the sacrifice of healthy animals, which, therefore, have not contracted the disease.

The invention here described thus presents a new vaccine formulation composed of the recombinant A2 protein, associated to adjuvants such as saponin, which is non-limiting and presents proven efficacy in inducing adequate protection and immune response—not only in experimental models, but also in dogs.

The formulation is composed of the A2antigen of *Leishmania*, produced in *Escherichia coli*, in the recombinant protein (or antigen) form. The qualitative and quantitative formulas contain:

Recombinant A 2 -HIS (rA2) . . . protein 50 to 200.00 μg/mL
Saponin . . . 0.125 to 0.500 mg/mL
q.s.p buffered saline solution . . . 1.00 mL
Thimerosal . . . 0.01 mL For the production of the recombinant A2 protein the coding sequence of this antigen was cloned in the pET protein expression vector. The BL21 *Escherichia coli* string was transformed, and thereby the A2 protein was expressed with a tail of six Histidine amino acids, which allows the purification of the recombinant protein through affinity chromatography for nickel. Electrophoresis tests in SDS-PAGE systems, Western-Blot tests and DNA sequencing confirmed the identity of the A2 protein cloned in *E. coli*. The expression of the Recombinant A2 protein (rA2) was obtained after the induction of the bacterial cultivation with 1.0 mM of IPTG (isopropyl-β-D-thiogalatopyranoside). The rA2 protein was purified through affinity chromatography in a column containing nickel ions. After being purified, the integrity and purity of the protein were assessed through the Immuno Blot technique. The adjustment of the protein's concentration per mL is done using the buffered saline solution containing 0.5 mg saponin and thimerosal.

The main innovation of the formulation of this vaccine is its capacity to induce cellular immune response in dogs, characterised by the induction in high levels of IFN-γ, and humoural immune response, characterised by the production of specific antibodies against the vaccine antigen that, yet, do not react to the non-soluble (brute) or soluble extract of the promastigote forms of *Leishmania* in the ELISA tests or in the immunofluorescence reaction.

This way, the dogs vaccinated with the vaccine formulation remain seronegative after each of the vaccine doses necessary to the immunisation process, allowing for the serologic distinction between animals vaccinated with A2 and those infected, which are seropositive in the ELISA tests, by means of the non-soluble (brute) or soluble extract of the parasites.

This way, dogs vaccinated with this vaccine formulation remain seronegative after each of the vaccine doses necessary to the immunisation process. It is thus possible to perform the serologic distinction between only vaccinated with A2 from those infected, which are seropositive in ELISA tests or in reaction with the brute or soluble parasite extract.

The results described above can be demonstrated by the following examples:

BRIEF DESCRIPTION OF THE DRAWINGS

FIG. 7 shows production of sub-classes IgGa and IgG2a.

EXAMPLE 1

Protection Levels Induced Against the Infection By *L. amazonensis* in BALB/c Mice Immunized with the A2 Antigen The immunisation with the A2 antigen, in the Recombinant A2 protein (rA2) form associated to rIL-12 as an adjuvant, or in the A2 DNA form, was effective in granting protection to BALB/c mice against the challenge-infection by *L. amazonensis*. In the assessment of the immunised and challenged animals a significant reduction of the average size of the wounds (FIG. 1) was observed, as well as a reduction in the parasite load (FIG. 2) in the infected paws.

Figure 1:
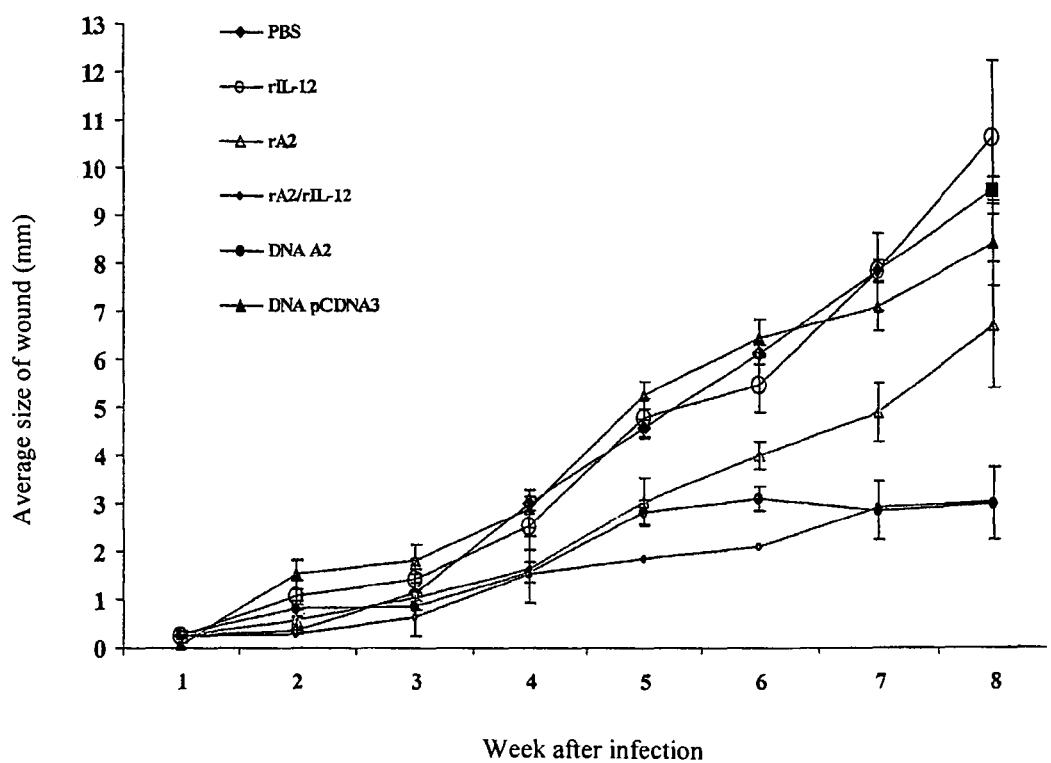
FIG. 1 shows average size of wounds.

FIG. 1 presents the evaluation of the average size of the wounds on the infected paws of BALB/c mice immunised with the Recombinant A2 protein (rA2), associated or not to rIL-12, to rIL-13, to A2 DNa or to pcDNA3 DNA and challenged with *L. amazonensis*. BALB/c mice groups (n=6, for example) were immunised with A2 DNA, in the left tibial muscle, in intervals of 21 days. Control groups received only PBS or were immunised with the empty plasmid (pcDNA3 DNA). As an adjuvant control, mice were also subcutaneously immunised with the rA2 protein, associated or not to rIL-12 or only with rIL-12. The mice were challenged with $1 \times 10^6$ *L. amazonensis* promastigotes in stationary growth phase, in the plantar fascia. The evolution of the wounds' size was monitored through weekly measurement of the width of the infected and the not infected paw. Each point represents the average, with the standard deviation added to or subtracted from it (in mm), obtained by the difference between the width of the infected and the not infected paw.

Figure 2:
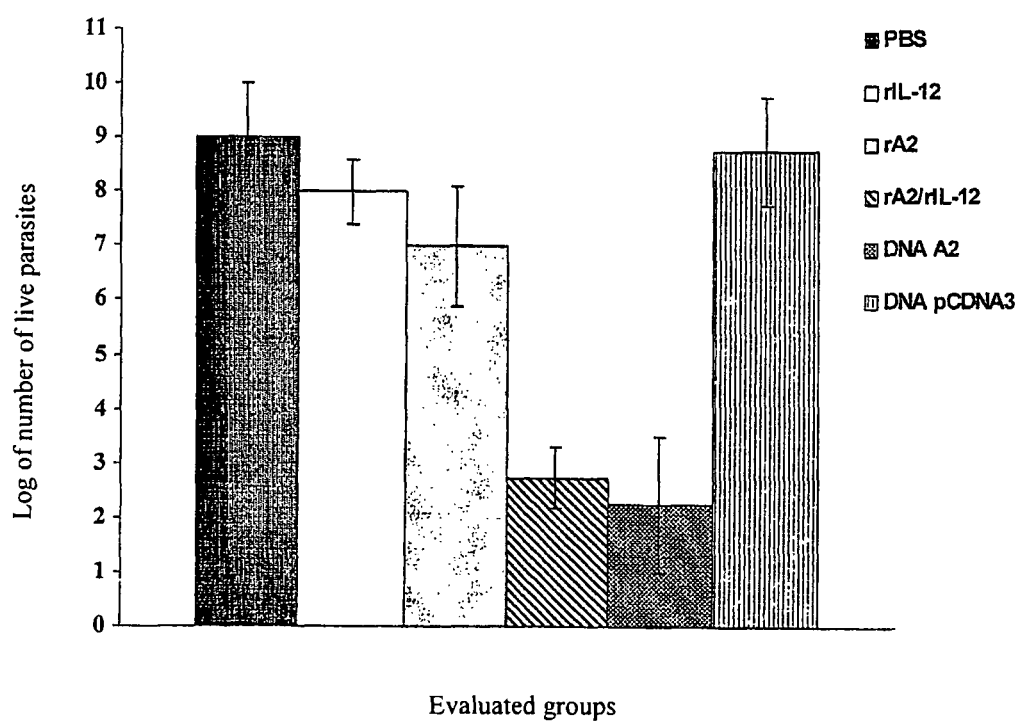
FIG. 2 shows number of live parasites.

FIG. 2 represents the Evaluation of the parasite load in the infected paws of BALB/c mice immunised with the recombinant A2 protein (rA2), associated or not to rIL-12, to rIL-13, to A2 DNa or to pcDNA3 DNA and challenged with *L. amazonensis*. BALB/c mice groups (n=6, for example) were immunised with 2 100 µg doses of A2 DNA, in the left tibial muscle, in intervals of 21 days. Control groups received only PBS or were immunised with the empty plasmid (pcDNA3 DNA). As an adjuvant control, mice were also subcutaneously immunised with the rA2 protein, associated or not to rIL-12 or only with rIL-12. 28 days after the last dose, the mice were challenged with $1 \times 10^6$ *L. amazonensis* promastigotes in stationary growth phase, in the plantar fascia. About eight weeks after the challenge-infection, the parasite load in the animals (n=4 per group) was determined by the limiting dilution technique, as described in the Material and Methods Section. Each bar represents the average, with the standard deviation added to or subtracted from it, corresponding to the logarithm of the number of parasites obtained by mg of tissue. Differences between the averages were verified by the Student-t test, being considered significant for p below 0.05.

EXAMPLE 2

Cellular and Humoural Immune Response in BALB/c Mice Immunised with the A2 Antigen and Challenged with *L. amazonensis*

Figure 3:
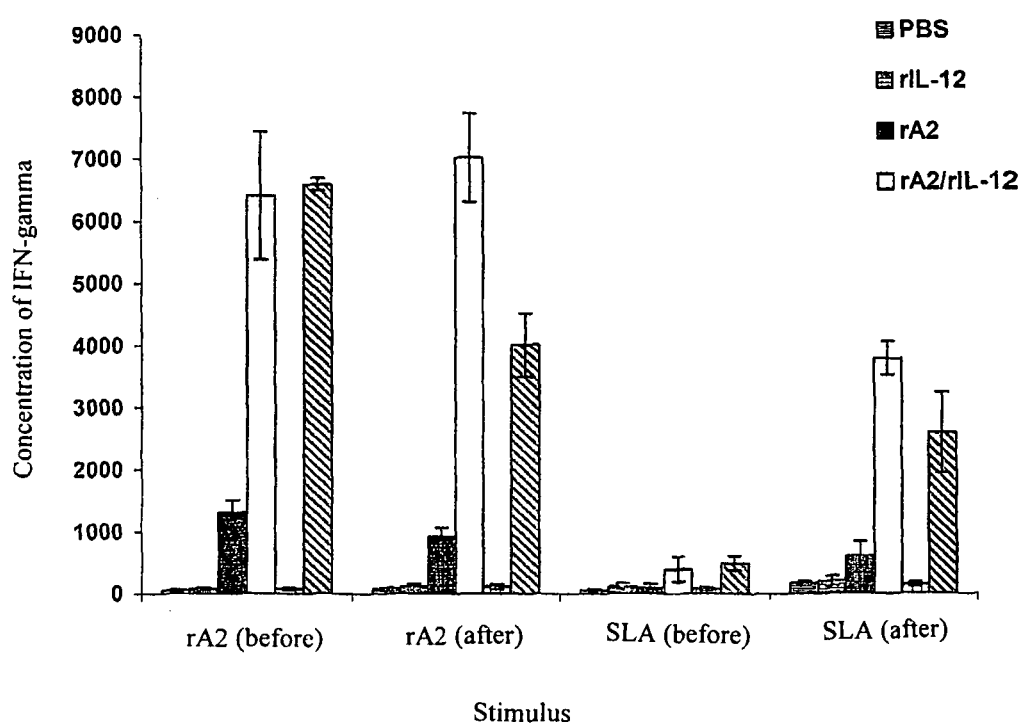
FIG. 3 shows production of IFN-gamma.

Animals immunised with A2 DNA or with rA2/rIL-12 and challenged with *L. (L.) amazonensis* presented significant production of IFN-γ after the in vitro stimulation of splenocytes with the rA2 protein or with the total extract of *L. (L.) amazonensis* promastigotes (SLA) (FIG. 3). In addition to this, low levels of IL-4 and IL-10 were observed in these groups, as compared to the control groups, after stimulation of the cells with the rA2 protein or with SLA of *L. (L.) amazonensis* (FIGS. 4 and 5).

FIG. 3 is a graph that represents the IFN-γ production by splenocytes of BALB/c mice immunised with the Recombinant A2 protein (rA2), associated or not to rIL-12, with rIL-12, A2 DNA or pcDNA3 DNA and challenged with *L. (L.) amazonensis*. Spleen cells of BALB/c mice were collected before the challenge-infection, or approximately eight to nine weeks after the challenge in the case of those immunised with *L. (L.) amazonensis*. As controls, non-stimulated cells or cells stimulated with concanavalin A (5 µg/ml) were assessed, in order to assess cellular viability. The cultivations were incubated for 48 hours in an oven at 37° C., with the presence of $CO_2$ at 5%. After this, the overfloat was collected and the IFN-γ production was determined by capture ELISA. The axis of abscissas indicates the stimulus used in cellular cultivation, and also the moment when the cells were collected: before or after the challenge-infection. The axis of ordinates indicates the concentration, in pg/ml, of IFN-γ. Each bar represents the average production of IFN-γ, with the standard deviation of each group added to or subtracted from it.

Figure 4:
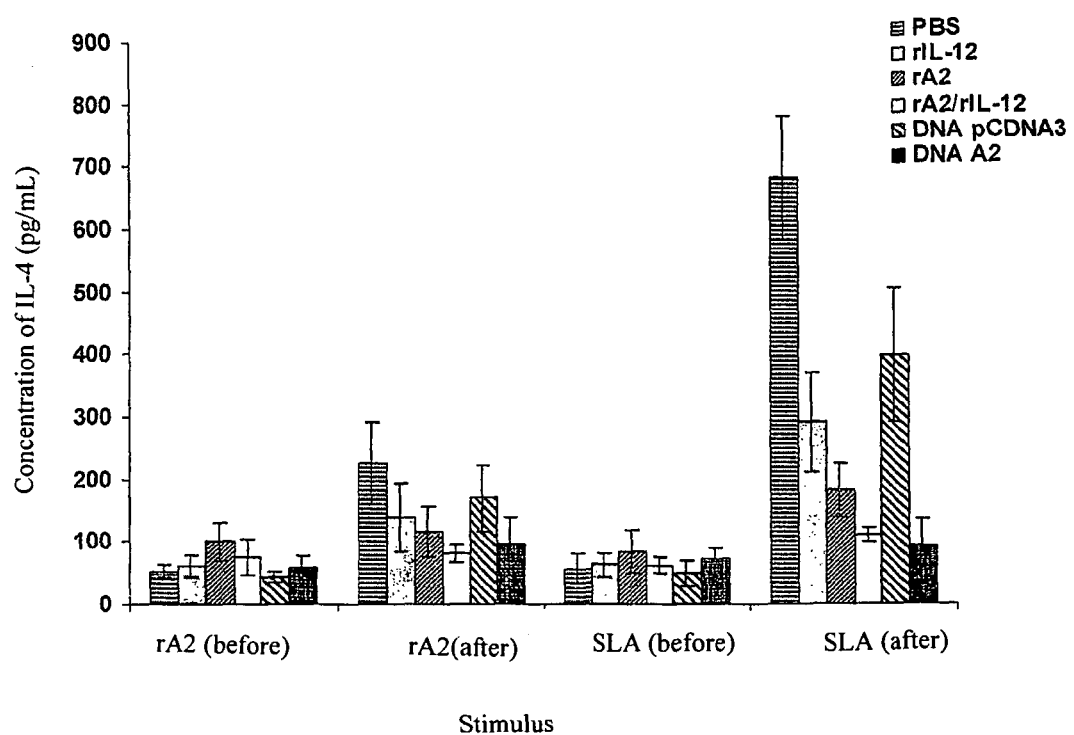
FIG. 4 shows production of interleukin-4.

FIG. 4 represents the IL-4 production by splenocytes of BALB/c mice immunised with the Recombinant A2 protein (rA2), associated or not to rIL-12, with rIL-12, A2 DNA or pcDNA3 DNA and challenged with *L. (L.) amazonensis*. Spleen cells of BALB/c mice were collected before the challenge-infection, or approximately eight to nine weeks after the challenge in the case of those immunised with *L. (L.) amazonensis*. The cells were cultivated ($1 \times 10^6$/ml) in 1 ml complete DMEM medium and stimulated with the rA2 protein (10 µg/ml) and with SLA of *L. (L.) amazonensis* (50 µg/ml). As controls, non-stimulated cells or cells stimulated with concanavalin A (5 µg/ml) were assessed, in order to assess cellular viability. The cultivations were incubated for 48 hours in an oven at 37° C., with the presence of $CO_2$ at 5%. After this, the overfloat was collected and the IL-4 production was determined by capture ELISA. The axis of abscissas indicates the stimulus used in cellular cultivation, and the moment when the cells were collected: before or after the challenge-infection. The axis of ordinates indicates the concentration, in pg/ml, of IL-4. Each bar represents the average production of IL-4, with the standard deviation of each group added to or subtracted from it.

Figure 5:
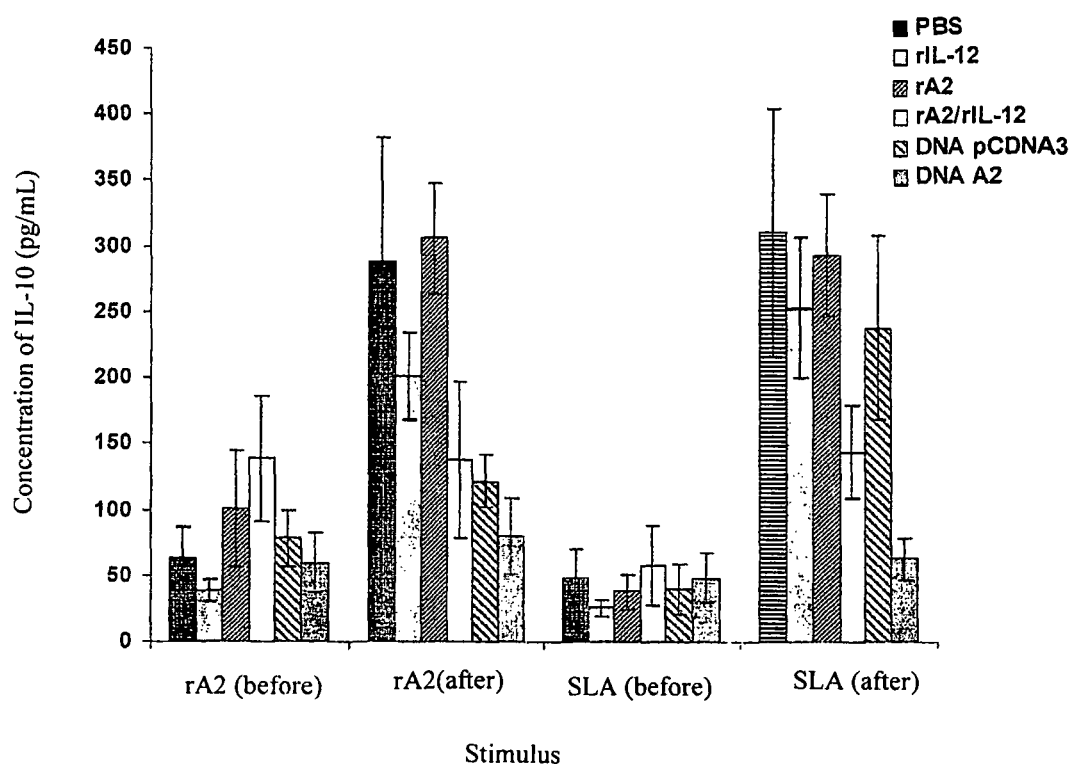
FIG. 5 shows production of interleukin-10.

FIG. 5 shows the graph representing the production of IL-1 by splenocytes of BALB/c mice immunised with the Recombinant A2 protein (rA2), associated or not to rIL-12, with rIL-12, A2 DNA or pcDNA3 DNA and challenged with L. (L.) amazonensis. Spleen cells of BALB/c mice were collected before the challenge-infection, or approximately eight to nine weeks after the challenge in the case of those immunised with L. (L.) amazonensis. The cells were cultivated ($1\times10^6$/ml) in 1 ml of complete DMEM medium and stimulated with the rA2 protein (10 µg/ml) and with SLA of L. (L.) amazonensis (50 µg/ml). As controls, non-stimulated cells or cells stimulated with concanavalin A (5 µg/ml) were assessed, in order to assess cellular viability. The cultivations were incubated for 48 hours in an oven at 37° C., with the presence of $CO_2$ at 5%. After this, the overfloat was collected and the IL-10 production was determined by capture ELISA. The axis of abscissas indicates the stimulus used in cellular cultivation, and the moment when the cells were collected: before or after the challenge-infection. The axis of ordinates indicates the concentration, in pg/ml, of IL-10. Each bar represents the average production of IL-10, with the standard deviation of each group added to or subtracted from it.

In the assessment of humoural immune response (FIG. 6), serum samples collected from animal immunised with rA2/mL-12 or with A2 DNA and challenged with L. amazonensis showed high production of IgG2a antibodies specific to the rA2 protein (anti-rA2) and low production of antibodies specific to the parasite (anti-SLA), as opposed to what was observed in control groups (COELHO et al. Infect. Immun.: 71, 2003; COELHO. PhD thesis in Immunology. Belo Horizonte: Instituto de Ciências Biológicas da UFMG, 2004).

Figure 6:
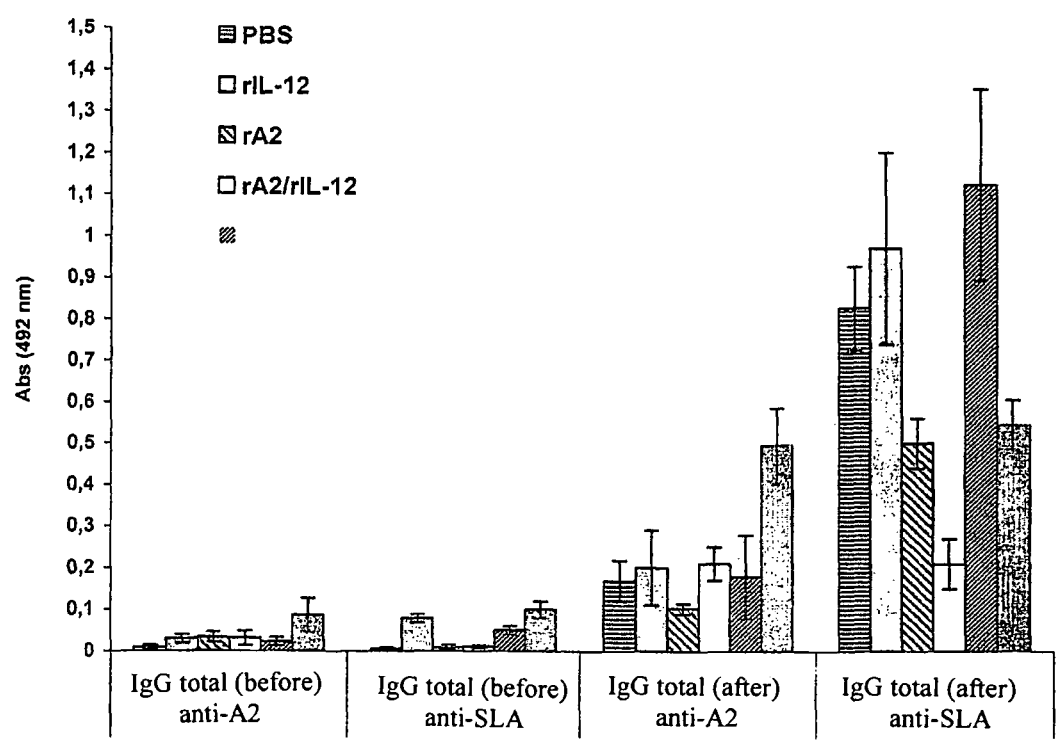
FIG. 6 shows production of total IgG.

FIG. 6 shows the production of total IgG in serum samples of BALB/c mice immunised with the Recombinant A2 protein (rA2), associated or not to rIL-12, with rIL-12, A2 DNA or pcDNA3 DNA and challenged with L. (L.) amazonensis. Serum samples of BALB/c mice were collected before the challenge-infection, or approximately eight to nine weeks after the challenge in the case of those immunised with L. (L.) amazonensis. The plates were sensitised with the rA2 protein (250ng/well) or with L. amazonensis SLA. The production of total IgG was determined by capture ELISA. On the axis of abscissas is the total IgG class specific to the rA2 protein or to the L. amazonensis SLA, and the moment when the samples were collected: before or after the challenge-infection. The axis of the ordinates shows the absorbency at wavelength of 492 nm. Each bar represents the average production of total IgG, with the standard deviation of each group added to or subtracted from it.

In the assessment of the sub-classes IgG1 and IgG2a specific to the rA2 protein or specific to antigens of the parasite (SLA), it can be observed (FIG. 7) that serum samples collected from animals immunised with rA2/rIL-12 or with A2 DNA and challenged with L. amazonensis were predominant in the production of IgG2a antibodies specific to the rA2 protein (anti-rA2), when compared to the levels of IgG1 anti-rA2 antibodies obtained. Animals immunised with A2 remained, however, seronegative in tests using antigens of promastigote form of Leishmania (SLA) (Coelho et al.,2003; Coelho, 2004).

Figure 7:
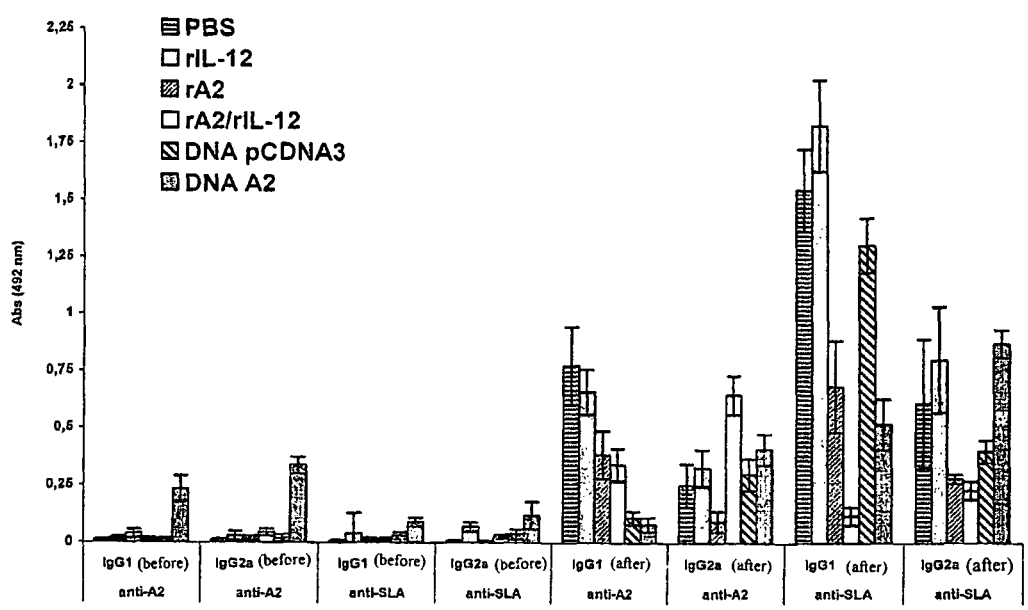

FIG. 7 describes the production of IgG1 and IgG2a in serum samples of BALB/c mice immunised with the Recombinant A2 protein (rA2), associated or not to rIL-12, with rIL-12, A2 DNA or pcDNA3 DNA and challenged with L. (L.) amazonensis. Serum samples of BALB/c mice were collected before the challenge-infection, or approximately eight to nine weeks after the challenge in the case of those immunised L. (L.) amazonensis. The plates were sensitised with the rA2 protein (250 ng/well) or with L. amazonensis SLA. The production of IgG1 and IgG2a was determined by capture ELISA. The axis of abscissas shows indications of the IgG1 and IgG2a sub-classes specific to the rA2 protein or specific to the L. amazonensis SLA, and the moment when the samples were collected: before or after the challenge-infection. The axis of the ordinates shows the absorbency at wavelength of 492nm. Each bar represents the average production of IgG1 or IgG2a, with the standard deviation of each group added to or subtracted from it.

EXAMPLE 3

Protection Levels Induced Against the Infection by L. chagasi in BALB/c Mice Immunised with the A2 Antigen The A2 antigen, when administered in the A2 DNA form, also proved to be effective in granting protection to BALB/c mice against the challenge-infection with L. chagasi, the main etiologic agent of Visceral Leishmaniasis in South American countries. The immunised and challenged animals displayed expressive reduction in the parasite load in the liver (FIG. 8) and in the spleen (FIG. 9).

Figure 8:
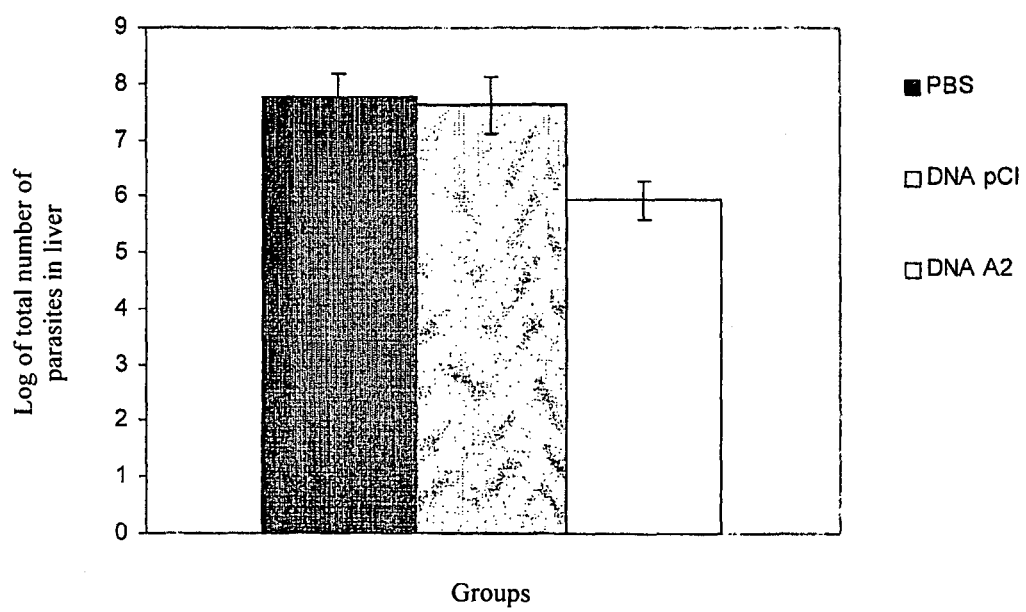
FIG. 8 shows number of parasites in liver.

FIG. 8: Assessment of the parasite load in the liver of BALB/c mice immunised with A2 DNA and challenged with L. chagasi. Groups of BALB/c mice (n=6 per group), after the immunisation protocols, were challenged with $1\times10^7$ L. chagasi promastigotes in stationary growth phase, by endovenous method, as described in the Material and Methods Section. Thirty-five days after the challenge the animals (n=4 per group) were sacrificed and the liver was recovered, in order to determine the parasite load. The bars represent the average log of the number of parasites per organ, with the standard deviation of each group added to or subtracted from it. The average log of the total number of parasites per organ was compared through a Student-t test. Statistical differences were considered significant for p lower than 0.05. There was a significant difference between the hepatic parasite load of animals from the A2 DNA group and those from the PBS group (p is lower than 0.0005) and from the pCI group (p is lower than 0.005).

Figure 9:
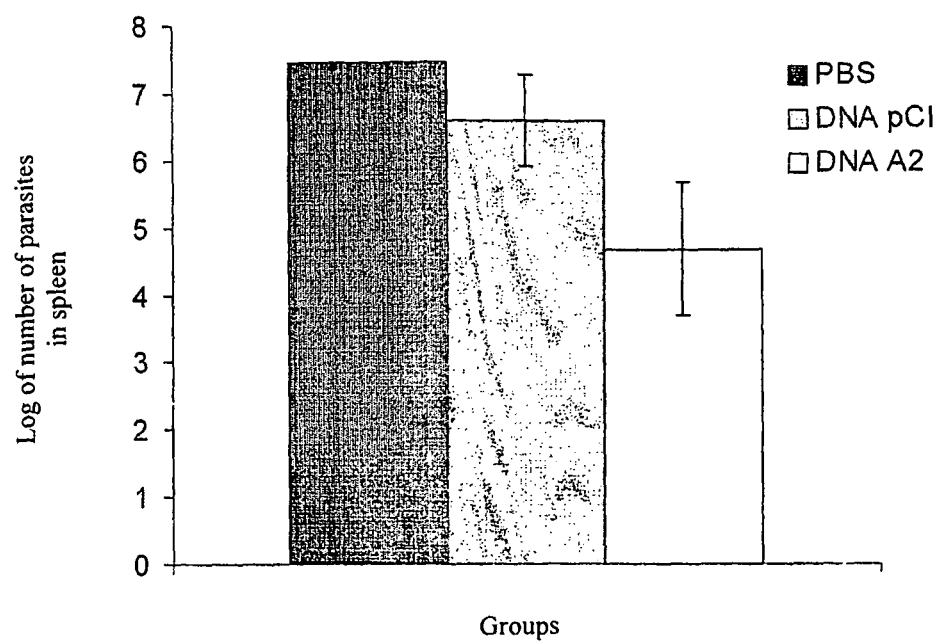
FIG. 9 shows number of parasites in spleen.

FIG. 9 shows the result of the assessment of the parasite load in the spleen of BALB/c mice immunised with A2 DNA and challenged with L. chagasi. Groups of BALB/c mice (n=6 per group), after the immunisation protocols, were challenged with $1\times10^7$ L. chagasi promastigotes in stationary growth phase, by endovenous method, as described in the Material and Methods Section. Thirty-five days after the challenge, the animals (n=4 per group) were sacrificed and the spleen was recovered, in order to determine the parasite load. The bars represent the average log of the number of parasites per organ, with the standard deviation of each group added to or subtracted from it. The average log of the total number of parasites per organ was compared through a Student-t test. Statistical differences were considered significant for p lower than 0.05. There was a significant difference between the spleen parasite load of animals from the A2 DNA group and those from the PBS and pCI groups (p is lower than 0.005 and 0.05, respectively).

EXAMPLE 4

Cellular Immune Response in BALB/c Mice Immunised with the A2 Antigen and Challenged with L. amazonensis BALB/c mice immunised with the A2 antigen, in the DNA form, and challenged with L. chagasi produced significantly higher levels of IFN-γ (FIG. 10) and significantly lower levels of IL-10 (FIG. 11) after the stimulus of the splenocytes with the rA2 protein or with the total extract of L. chagasi proteins (LcPA), as compared to the animals from the control group.

Figure 10:
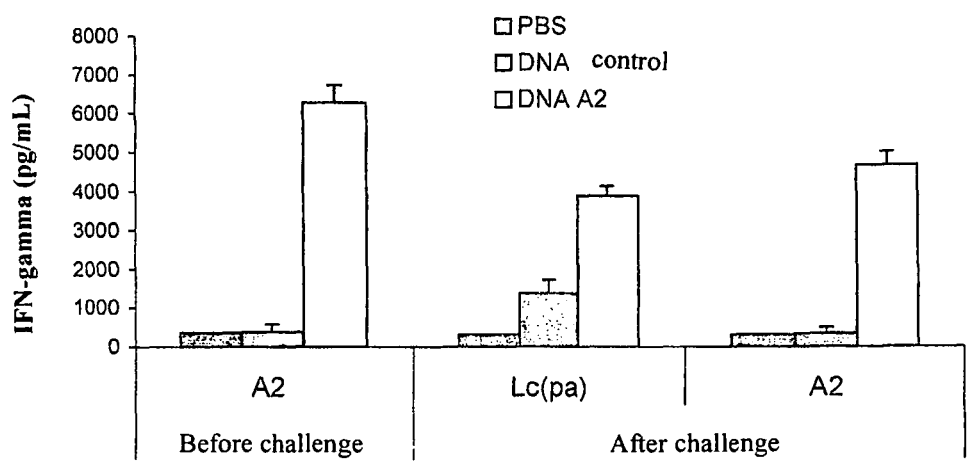
FIG. 10 shows production of IFN-gamma.

FIG. 10: graph of the production of IFN-γ by splenocytes of BALB/c mice immunised with A2 DNA before and after the challenge with *L. chagasi*. Spleen cells of immunised BALB/c mice were collected four weeks after immunisation or approximately nine weeks after infection with *L. chagasi*. The cells ($2\times10^5$ cells per ml) were cultivated in full DMEM and stimulated with the rNH, rA2 or rLACK recombinant proteins (concentrations of 10 μg/mL) or with the protein extract from *L. chagasi* (50 μg/mL). The overfloats were collected 48 hours after the cultivation and stimulation of the cells. The production of IFN-γ was determined by capture ELISA. The axis of the abscissas indicates the stimuli used in cellular cultivation, and the axis of the ordinates indicates the concentration of IFN-γ (pg/mL). Each bar represents the average, with the standard deviation of each group's IFN-γ production added to or subtracted from it. The IFN-γ base production is 428.0, to which is added or subtracted 66.45 pg/mL. (*) indicates significant difference in relation to the PBS and DNA control groups, evaluated by the Student-t test. The values are considered significant for p lower than 0.05.

Figure 11:
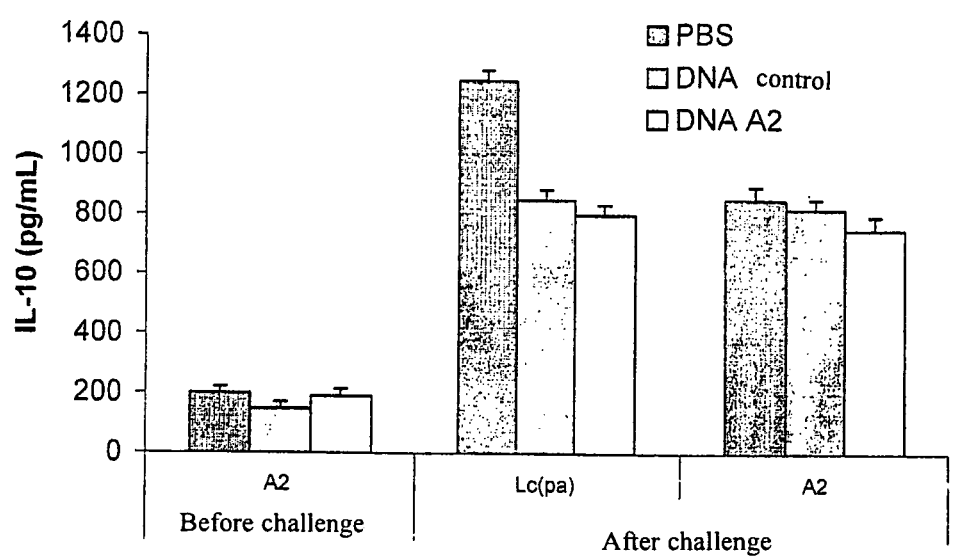
FIG. 11 shows production of interleukin-10.

FIG. 11 shows the production of IL-10 by splenocytes of BALB/c mice immunised with plasmids of AH DNA, A2 DNA, LACK DNA or their associations before and after the challenge with *L. chagasi*. Groups of BALB/c mice (n=6 per group), after the immunisation protocols, were challenged with $1\times10^7$ *L. chagasi* promastigotes in stationary growth phase, by endovenous method, as described in the Material and Methods Section. Twenty-eight days after the immunisation or thirty-five days after the challenge-infection the spleen cells were cultivated in complete DMEM medium and stimulated with the rNH, rA2 or rLACK recombinant proteins (of 10 μg/mL) or with the soluble extract from *L. chagasi* (LcPA, 50 μg/mL). The overfloats were collected 48 hours after the cultivation and stimulation of the cells. The production of IFN-γ was determined by capture ELISA. The axis of the abscissas indicates the stimuli used in cellular cultivation, and the axis of the ordinates indicates the concentration of IL-10 (pg/mL.) Each bar represents the average IL-10 production, with each group's standard deviation added to or subtracted from it. The IL-10 base production is 653.5, to which is added or subtracted 59.6 pg/mL. (*) indicates significant difference in relation to the PBS group and (**) indicates that there is significant difference in relation to both the PBS and DNA groups. The statistical analysis is done by the Student-t test. The values are considered significant for p lower than 0.05.

EXAMPLE 5

Cellular and Humoural Immune Response Induced by Immunisation with the A2 Antigen in Beagle Dogs Beagle dogs were divided in groups and immunised with three doses of the A2/saponin vaccine formulation in intervals of 21 days, by subcutaneous method, according to the immunisation protocol described below. As controls, groups of animals were immunised with an adjuvant (saponin), or received only PBS.

| GROUPS | IMMUNISATION METHOD |
|---|---|
| GROUP 1 (n = 17) | A2 antigen |
| GROUP 2 (n = 7) | Saponin |
| GROUP 3 (control) (n = 7) | Phosphate Buffered Saline (PBS) |

After the administration of each dose, the humoural response was assessed by determination of the total IgG antibodies level through the ELISA method. It was also assessed by the determination of the IgG1 and IgG2 isotypes, which are indirect markers of the induction of Th2 and Th1 cellular response, respectively. The level of antibodies produced against the vaccine antigen and against the total extract of antigens of total promastigote forms (classic VL diagnosis method) was assessed.

Figure 12:
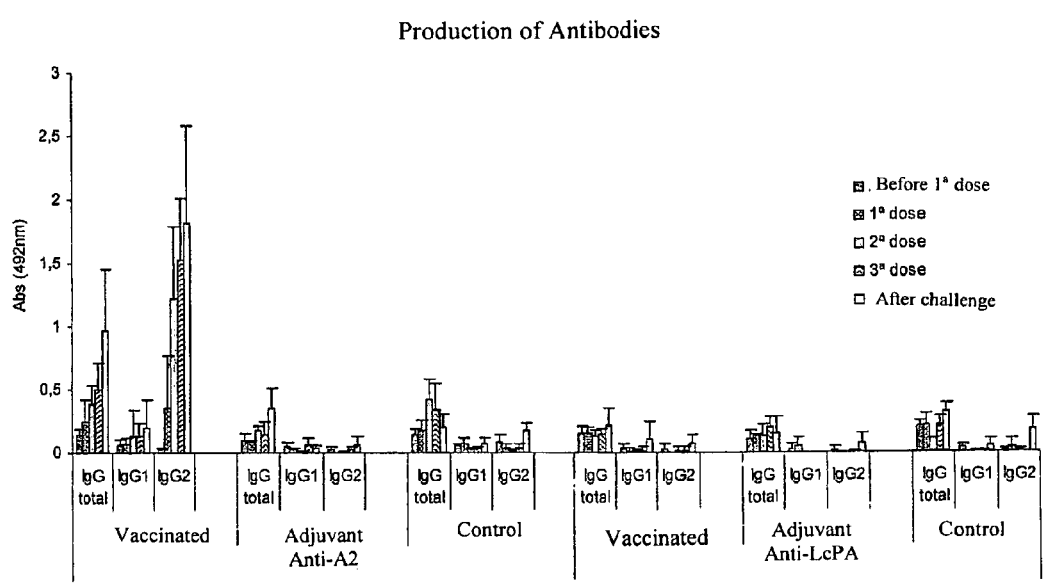
FIG. 12 shows production of antibodies.
Figure 13:
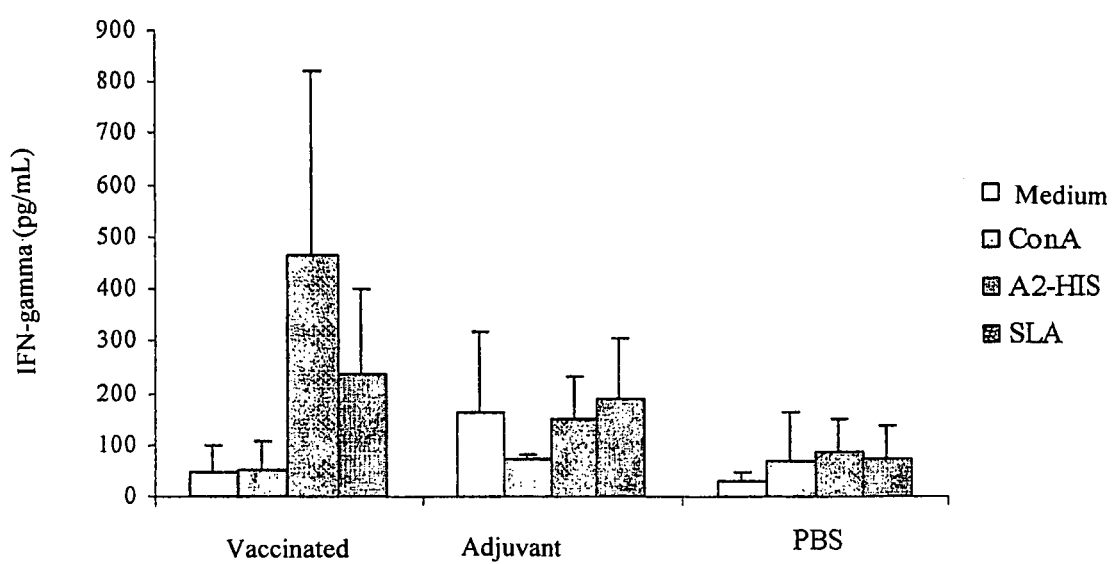
FIG. 13 shows production of IFN-gamma.

As it can be seen in FIGS. 12 and 13, animals vaccinated with the vaccine formulation present serologic reaction against the vaccine antigen, but remain seronegative in the reaction with the total parasite extract. As a result, it is possible to perform serologic distinction between the animals only vaccinated with A2 and those) infected, which are seropositive in ELISA tests, in a reaction with the non-soluble (brute) or soluble extract of the parasites.

Therefore, the main innovation of this vaccine formulation is its capacity to induce humoural immune response in dogs. This is characterised by the production of antibodies specifically against the vaccine antigen, which, however, do not react with the non-soluble (brute) or soluble extract of the promastigote forms of *Leishmania* in the ELISA tests or in the immunofluorescence reaction (data not presented).

FIG. 12 presents a graph with the levels of total IgG, IgG1 and IgG2 antibodies in serum samples from dogs, before and after each dose of the immunisations as wells as before and after the challenge-infection with *L. chagasi*. The ELISA plates were sensitised with the Recombinant A2 protein (250 ng) or with *L. chagasi* LcPA (1 μg/well). Total IgG production was determined by direct ELISA; IgG1 and IgG2 production was determined by indirect ELISA. The axis of the ordinates represents absorbency at wavelength of 492 nm. On the axis of the abscissas, each bar indicates the average production of total IgG and of the IgG1 and IgG2 sub-classes, with each group's standard deviation added to or subtracted from it.

The part of the invention herein described refers to the production of IFN in response to the vaccine antigen. The cellular immune response was assessed by means of the IFN-γ dosage through the capture ELISA, after collecting and cultivating the peripheral blood mononuclear cells (PBMC) in vitro and stimulating them with the recombinant A2-HIS protein or with the *L. chagasi* soluble extract (LcPA). The cells were also stimulated with concanavalin A (ConA), as a control for cellular viability. In addition to this, a basal control was made, in which the cells were not stimulated.

As can be seen in FIG. 13, the animals immunised with the A2 antigen/saponin vaccine composition produced significantly higher levels of IFN-γ in cellular cultivations stimulated with the recombinant A2 protein, as compared to the groups "Control" (p=0.003926799) and "Adjuvant" (p=0.018896129), under the same stimulus. Comparing the IFN-γ production of the dog groups assessed in the non-stimulated cellular cultivations and in the cultivations stimulated with LcPA and with ConA, statistically significant differences were not found. In addition to this, the production was significantly higher in the cells stimulated with the A2-HIS protein, as compared to the non-stimulated ones (p=0.001374901), to the ones stimulated with ConA (p=0.00199055) or to the ones stimulated with LcPa (p=0.015277637)—assessing the group immunised with the A2 antigen/saponin vaccine composition. Statistically significant differences were not found inside the "Adjuvant" and "Control" groups under the same stimulus (FIG. 13).

The animals of the "Vaccinated" group displayed significantly higher production of IgG2, specific to the rA2, as compared to IgG1, before and after the challenge infection with *L. chagasi* (p=0.0000000004 and p=0.0000000615, respectively). This was also observed in the "Control" group, after the challenge infection (p=0.0341668528). Dogs of the "Vaccinated" group, before and after the challenge-infection, displayed a IgG1/IgG2 ratio smaller than 1, which is an indicative of Th1 response (0.12224007 and 0.1085985, respectively) (Table 1). The dogs of the "Adjuvant" and "Control" groups, on the other hand, produced really low quantities of these antibodies (FIG. 12). The IgG1/IgG2 ratios, before and after the infection, are 2.1096344 and 0.52443 for the "Adjuvant" group, and 0.9171905 and 0.4106352 for the "Control" group (Table 1).

TABLE 1

Ratio of the IgG1/IgG2 sub-classes in serum samples of dogs immunised with the rA2 protein (vaccinated) and of dogs from the Adjuvant and Control groups (PBS), before and after the challenge-infection (period of one month) with *L. chagasi*. The plates were sensitised with the recombinant A2-HIS protein (250 ng) or with *L. chagasi* LcPA (1 μg/well). The production of the IgG1 and IgG2 sub-classes was determined by indirect ELISA.

| | Sensitising Agent A2-HIS PROTEIN | |
|---|---|---|
| Assessed group | Before the challenge | After the challenge |
| Vaccinated | 0.122241 | 0.108599 |
| Adjuvant | 2.109744 | 0.52443 |
| Control | 0.917787 | 0.410635 |

These results show that the vaccine formulation induces the development of Th1 response, which relates to the profile observed in asymptomatic or infection-resistant dogs (Pinelli et al., 1994; Quinnell et al., 2001; Santos-Gomes et al., 2002).

FIG. 13 displays a graph representing the production of IFN-γ by peripheral blood mononucleated cells (PBMC) from Beagle dogs immunised with the A2 antigen/saponin vaccine formulation, before the challenge-infection with *L. chagasi*. The cells were cultivated ($1\times10^6$/ml) in one ml of complete DEMEM medium and stimulated with the recombinant A2 protein (10 μg/mL) and with *L. chagasi* LcPA, at 50 μg/mL concentration. As the control, non-stimulated cells (Middle) were assessed. Concanavalin A (2.5), a mitogen, was also used as a control to assess cellular viability. The cultivations were incubated in an oven at 37° C., with 5% $CO_2$. After 48 hours the overfloat was collected and the IFN-γ production was determined by capture ELISA. The axis of the ordinates represents the concentration, in pg/ml, of IFN-γ. The axis of the abscissas shows the dog groups, where "Vaccinated" corresponds to the group of dogs which received the A2 antigen/saponin vaccine formulation, "Adjuvant" corresponds to the group which received only the adjuvant, and "Control" to the group that received PBS. Each bar represents the average IFN-γ production and each group's standard deviation. * indicates significant difference between the Vaccinated and Adjuvant (A2-HIS) groups, p=0.018896129. ** indicates significant difference between the Vaccinated and Control (A2-HIS) groups, p=0.003926799; Student-t test (Excel).

What is claimed is:

1. A recombinant vaccine against leishmaniasis comprising a recombinant A2 protein of amastigote forms of *Leishmania* that allows serologic distinction between vaccinated and infected animals by conventional serologic tests, ELISA and immunofluorescence using antigens of promastigote forms selected from the group consisting of *Leishmania amazonensis, L. donovani, L. infantum,* and *L. chagasi;* wherein the recombinant vaccine contains: (i) recombinant A2-HIS (rA2) protein from 50 μg/mL to 200 μg/mL and saponin from 0.125 mg/mL to 0.500 mg/mL in a buffered saline solution and (ii) 0.01 mL of thimerosal per 1.00 mL of the buffered saline solution.

2. The recombinant vaccine as claimed in claim 1, characterized by inducing humoral and cellular immune responses in a dog through production respectively of antibodies against A2 antigen and elevated levels of IFN-γ.

3. A method to enhance immune response against leishmaniasis, comprising administering the composition as claimed in claim 1.

4. A method to enhance immune response against leishmaniasis, comprising administering the composition as claimed in claim 2.

5. A pharmaceutical composition comprising a recombinant A2 protein of amastigote forms of *Leishmania*, an adjuvant, at least one pharmaceutically acceptable excipient, a buffer, and a preservative; wherein the recombinant A2 protein is at a concentration from 50 μg/mL to 200 μg/mL.

6. The composition as claimed in claim 5, which comprises saponin as adjuvant.

7. The composition as claimed in claim 6, wherein the saponin is at a concentration from 0.125 mg/mL to 0.500 mg/mL.

8. The composition as claimed in claim 5, wherein the pharmaceutically acceptable excipient comprises saline, dextrose, water, or a combination thereof.

9. The composition as claimed in claim 5, which comprises buffered saline solution as buffer.

10. The composition as claimed in claim 5, which comprises thimerosal as preservative.

11. A method to enhance immune response against leishmaniasis, comprising administering the composition as claimed in claim 5.

12. A method to enhance immune response against leishmaniasis, comprising administering the composition as claimed in claim 6.

13. A method to enhance immune response against leishmaniasis, comprising administering the composition as claimed in claim 10.

14. A method to enhance immune response against leishmaniasis, comprising administering the composition as claimed in claim 7.

15. A method to enhance immune response against leishmaniasis, comprising immunization with a pharmaceutical composition comprising recombinant A2 protein of amastigote forms of *Leishmania* in three doses at different intervals; wherein the pharmaceutical composition is comprised of recombinant A2 protein at a concentration from 50 μg/mL to 200 μg/mL.

16. The method according to claim 15, characterized by inducing humoral and celular immune responses in a dog through production respectively of antibodies against A2 antigen and elevated levels of IFN-γ.

17. The method according to claim 15, wherein the pharmaceutical composition is further comprised of saponin at a concentration from 0.125 mg/mL to 0.500 mg/mL.

* * * * *